(12) United States Patent
Delnevo

(10) Patent No.: US 7,361,267 B2
(45) Date of Patent: Apr. 22, 2008

(54) DIALYSIS MACHINE BLOOD CIRCULATING CIRCUIT FITTING

(75) Inventor: Annalisa Delnevo, Correggio (IT)

(73) Assignee: Gambro Dasco S.p.A., Medolla (IT)

( * ) Notice: Subject to any disclaimer, the term of this patent is extended or adjusted under 35 U.S.C. 154(b) by 1258 days.

(21) Appl. No.: 10/312,386

(22) PCT Filed: Mar. 4, 2002

(86) PCT No.: PCT/IT02/00131

§ 371 (c)(1), (2), (4) Date: Dec. 26, 2002

(87) PCT Pub. No.: WO02/070041

PCT Pub. Date: Sep. 12, 2002

(65) Prior Publication Data

US 2004/0019314 A1  Jan. 29, 2004

(51) Int. Cl.
*B01D 61/32* (2006.01)

(52) U.S. Cl. ............ 210/85; 210/90; 210/321.6; 210/541; 210/646; 138/30; 138/89; 138/104; 285/93; 604/5.01; 604/65; 604/67

(58) Field of Classification Search ............ 210/85, 210/90, 94, 96.2, 321.6, 95, 646, 541; 285/93, 285/374, 399; 600/488; 138/30, 89, 104; 604/4.01, 5.01, 6.01, 6.09
See application file for complete search history.

(56) References Cited

U.S. PATENT DOCUMENTS

| | | | | |
|---|---|---|---|---|
| 4,077,882 A | * | 3/1978 | Gangemi | 210/90 |
| 4,214,779 A | * | 7/1980 | Losell | 285/93 |
| 4,745,279 A | | 5/1988 | Karkar et al. | |
| 5,158,091 A | * | 10/1992 | Butterfield et al. | 600/485 |
| 6,039,078 A | * | 3/2000 | Tamari | 138/30 |
| 6,171,253 B1 | * | 1/2001 | Bullister et al. | 600/486 |
| 7,074,191 B2 | * | 7/2006 | Bosetto et al. | 600/488 |

FOREIGN PATENT DOCUMENTS

| | | |
|---|---|---|
| EP | 1 078 642 A2 | 2/2001 |
| JP | 63221221 | 9/1988 |
| JP | 9024026 | 1/1997 |
| JP | 11226119 | 8/1999 |
| JP | 2000060965 | 2/2000 |

\* cited by examiner

*Primary Examiner*—Joseph Drodge
(74) *Attorney, Agent, or Firm*—Finnegan, Henderson Farabow, Garrett & Dunner, L.L.P.

(57) ABSTRACT

A fitting (1) for a blood circulating circuit (4) of a dialysis machine has a first ans a second mouth (8, 9) for connecting the fitting (1) to a first ans a second portion (2, 3) of the blood circulating circuit (4) respectively; the fitting (1) defining a third portion (10) of the blood circulating circuit (4) by means of a tuby (6) by which to determine the absorption of electromagnetic waved by the blood, and by means of a chamber (7) having a wall (15) movable as a function of the pressure of the blood.

10 Claims, 2 Drawing Sheets

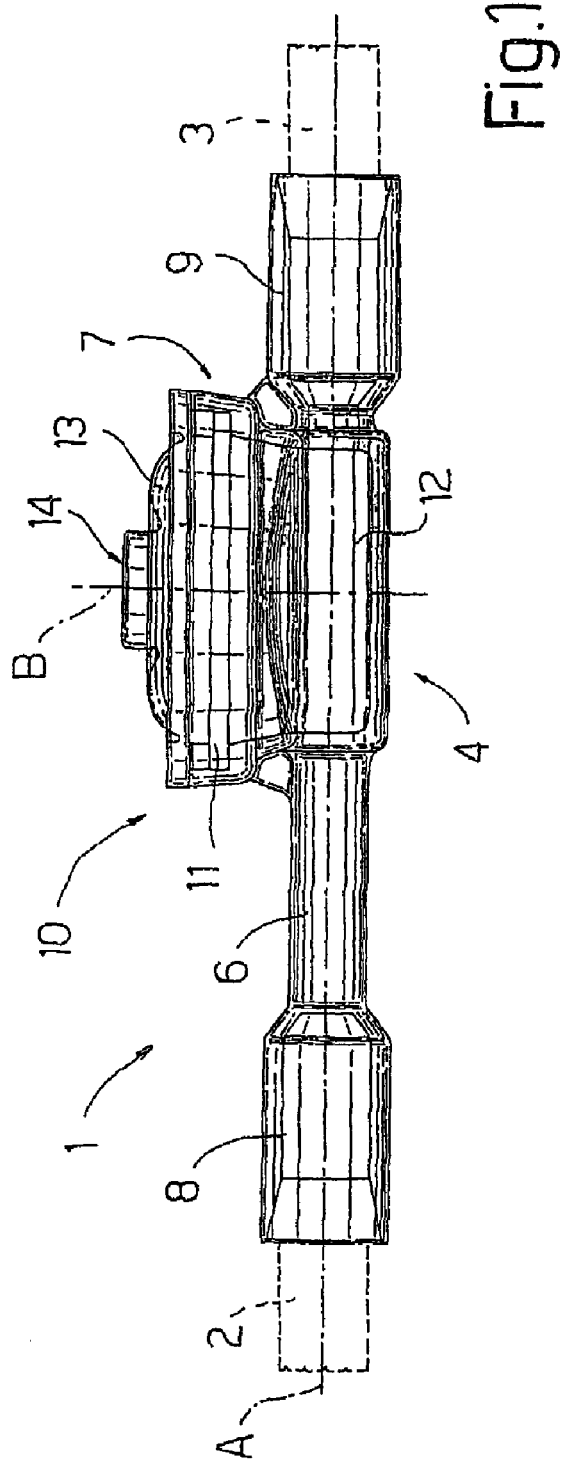
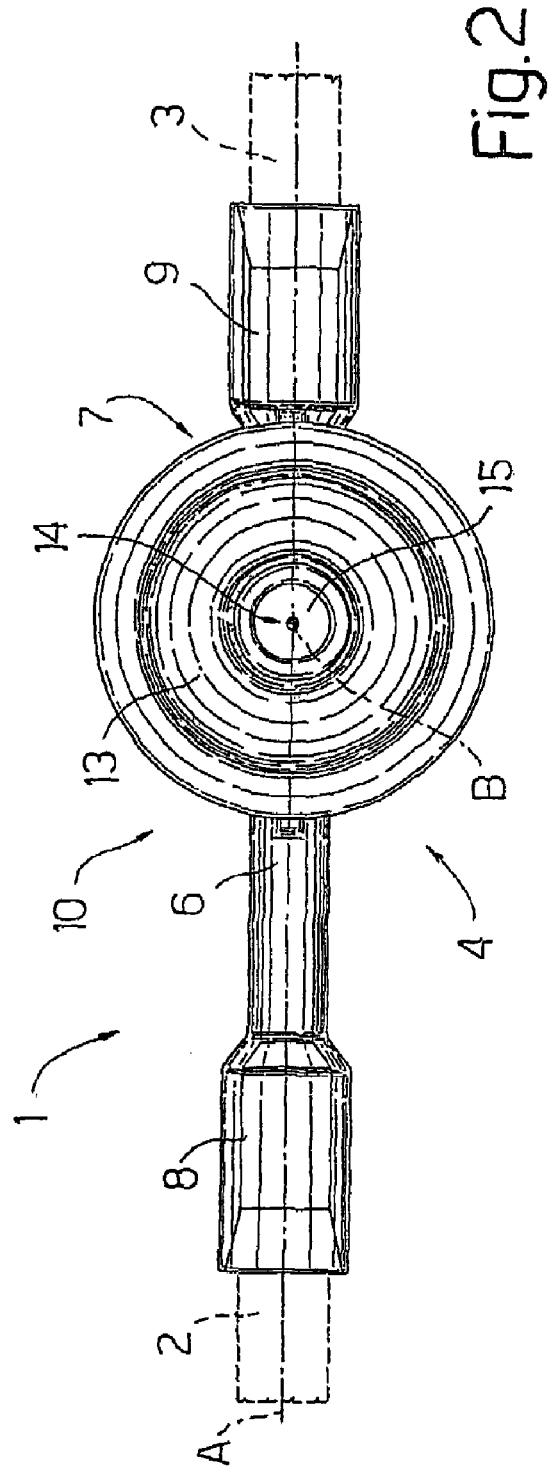

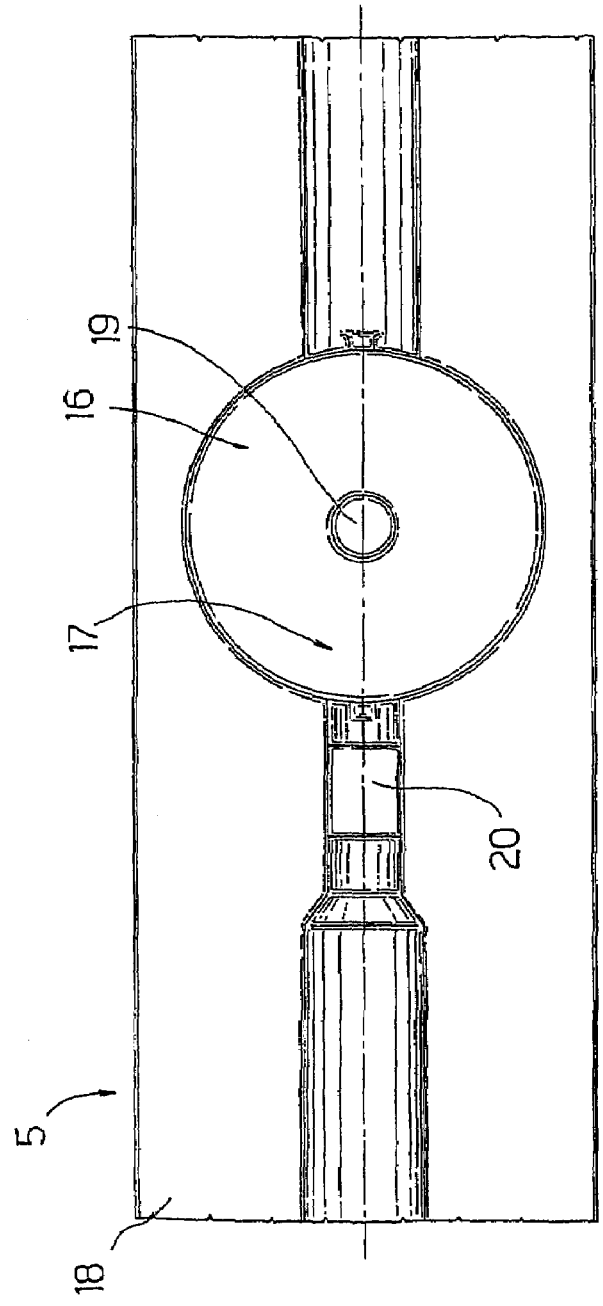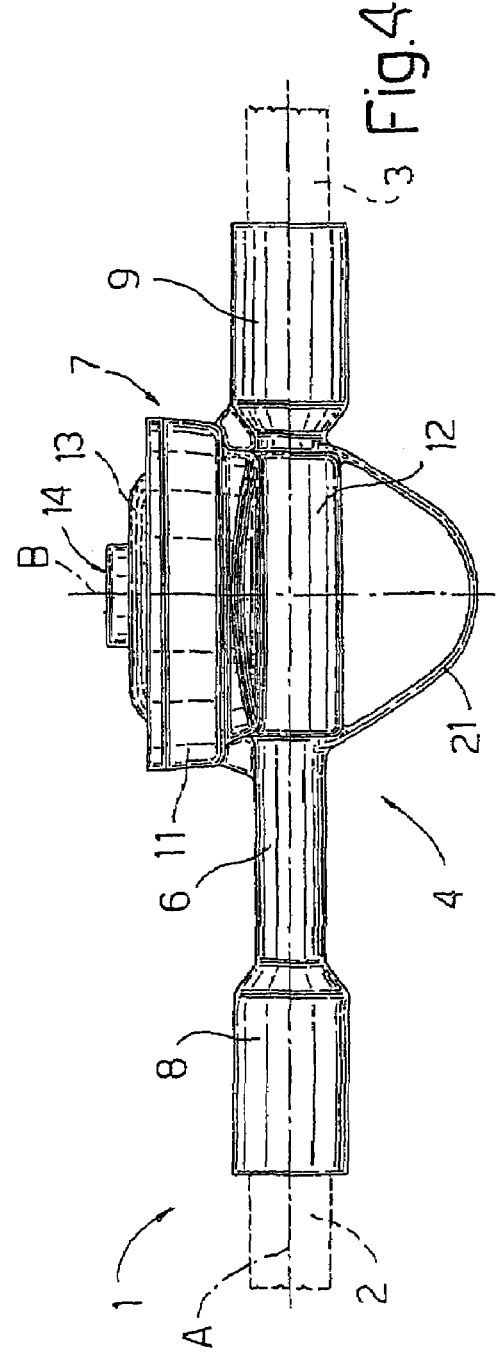

DIALYSIS MACHINE BLOOD CIRCULATING CIRCUIT FITTING

TECHNICAL FIELD

The present invention relates to a dialysis machine circuit fitting.

BACKGROUND ART

Known dialysis machines normally comprise a blood circulating circuit connected, in use, to the patient's circulatory system; a treatment fluid circulating circuit; and a filter, through which the blood circulating circuit feeds the blood, and the treatment fluid circulating circuit feeds the treatment fluid. The filter comprises a semipermeable membrane for separating, in use, the treatment fluid from the blood, so that ions are exchanged between the treatment fluid and the blood, and part of the plasma in the blood is transferred through the membrane. The blood circulating circuit comprises an arterial branch upstream from the filter, and a venous branch downstream from the filter, and the machine comprises a peristaltic pump located along the arterial branch to feed the patient's blood to the filter. The blood circulating circuit and second the treatment fluid circulating circuit are made of transparent, flexible material, such as PVC, which ensures sterility of the circuits. The flexibility of the circuits simplifies packaging and enables flow to be cut off by simply constricting a portion of the circuit, while transparency enables visual monitoring of liquid flow in the circuit.

During the dialysis treatment itself, certain physical characteristics of the blood along the first circuit are determined non-invasively to monitor treatment and possibly also adjust dialysis parameters. This is normally done by means of pressure sensors and sensors for detecting the absorption of electromagnetic waves by the blood. Such sensors are provided on the dialysis machine and are connected to specific points along the first circuit, which is used for one dialysis treatment only and then disposed of as controlled waste.

DISCLOSURE OF THE INVENTION

It is an object of the present invention to provide a circuit fitting enabling troublefree, non-invasive monitoring of physical characteristics of the blood during dialysis.

According to the present invention, there is provided a fitting for a blood circulating circuit of a dialysis machine, the fitting comprising a first and a second mouth for connecting the fitting to a first and a second portion of the blood circulating circuit respectively; said fitting defining a third portion of said blood circulating circuit; and the fitting being characterized by comprising a tube by which to determine the absorption of electromagnetic waves by the blood; and a chamber having a wall movable as a function of the pressure of the blood.

The present invention also relates to a measuring device.

According to the present invention, there is provided a measuring device designed to cooperate with a blood circulating circuit comprising a fitting; the measuring device being characterized by comprising a seat for housing said fitting.

BRIEF DESCRIPTION OF THE DRAWINGS

A non-limiting embodiment of the present invention will be described by way of example with reference to the accompanying drawings, in which:

FIG. 1 shows a side view of a fitting in accordance with the present invention;

FIG. 2 shows a plan view of the FIG. 1 fitting;

FIG. 3 shows a schematic front view, with parts removed for clarity, of a measuring device in accordance with the present invention;

FIG. 4 shows a side view of a variation of the FIG. 1 fitting.

BEST MODE FOR CARRYING OUT THE INVENTION

Number 1 in FIGS. 1 and 2 indicates a fitting located between two portions 2 and 3 of a blood circulating circuit 4 of a dialysis machine (not shown). Fitting 1 is designed for connection to a measuring device 5 shown in FIG. 3, and comprises a tube 6 extending along an axis A; and a chamber 7, which is adjacent to and integral with tube 6, is located substantially on one side of axis A, and is substantially cylindrical with an axis B perpendicular to axis A. Fitting 1 comprises a mouth 8 for connection to portion 2; and a mouth 9 for connection to portion 3.

In other words, fitting 1 defines a portion 10 of circuit 4 extending between portions 2 and 3, which are made of transparent, flexible material, normally PVC. Tube 6 and chamber 7 communicate directly to allow the blood to flow, in use, along fitting 1.

With reference to FIG. 2, tube 6 has a diameter D1, while chamber 7, viewed from above, is circular with a diameter D2 larger than diameter D1, and comprises a cup 11 communicating on one side with tube 6 and on the opposite side with mouth 9. Cup 11 has a channel-shaped bottom 12 extending along axis A and connected to tube 6 and to mouth 9. Chamber 7 also comprises a cover 13 with a central hole 14; and an elastic membrane 15 gripped between cup 11 and cover 13 to close cup 11. Cup 11, tube 6, and mouths 8 and 9 are formed in one piece of rigid, transparent material, which is connected to membrane 15 and cover 13.

Cover 13 is made of the same material as tube 6 and cup 11, while membrane 15 is made of elastic material so as to flex alongside variations in the pressure of the blood.

Tube 6, being used to measure the absorption of electromagnetic waves, which are affected greatly, for example, by the diameter D1 and the thickness of tube 6, is made to conform as closely as possible to nominal dimensions.

With reference to FIG. 3, the measuring device 5 is integral with the machine (not shown), and has a seat 16 defined by a recess 17 formed in the body 18 of device 5. Recess 17 has a contour substantially identical with that of fitting 1 viewed from above, and is deep enough to house fitting 1 in seat 16 with cover 13 facing seat 16. Device 5 comprises two sensors having respective interfaces 19 and 20 housed in seat 16 and co-operating with fitting 1. More specifically, interface 19 forms part of a pressure sensor (not shown), and co-operates with membrane 15 to determine deformation of membrane 15 and enable the pressure sensor to generate a signal related to the pressure of the blood flowing through fitting 1.

Interface 20 forms part of a sensor for determining the absorption of electromagnetic waves by the blood along tube 6, and comprises electromagnetic wave emitters and detectors.

Seat 16 is defined by a groove for housing tube 6 and partly housing circuit 4; and by an opening negatively reproducing the shape of chamber 7. Seat 16 is shaped to provide for foolproof connection of fitting 1 and measuring device 5, so that interface 19 fits accurately inside hole 14, and interface 20 accurately about tube 6.

In actual use, when circuit 4 is connected in known manner to the dialysis machine, fitting 1 is inserted inside seat 16 and fixed to measuring device 5. During dialysis treatment, the blood flows through fitting 1 and deforms membrane 15, which is detected by interface 19 inserted inside hole 14. At the same time, electromagnetic wave absorption by the blood flowing through fitting 1 is detected by interface 20.

In the FIG. 4 variation, fitting 1 comprises a gripping member 21, which is connected to tube 6 at channel 12 of chamber 7, is located on the opposite side of axis A to cover 13, is arc-shaped, and is formed in one piece with tube 6 and cup 11.

Gripping member 21 provides for further simplifying insertion and removal of the fitting 1 inside and from seat 16.

The invention claimed is:

1. A fitting for a blood circulating circuit of a dialysis machine, the fitting comprising:
    a first and a second mouth for connecting the fitting to a first and a second portion of the blood circulating circuit, respectively; said fitting defining a third portion of said blood circulating circuit;
    a tube— and connected measuring device— configured to determine the absorption of electromagnetic waves by the blood flowing through said fitting, said tube being made of rigid and transparent material; and
    a chamber having an elastic membrane movable as a function of the pressure of the blood flowing through said fitting; said chamber comprising a cup formed in one piece with said tube; said chamber comprising a cover for gripping said elastic membrane between said cup and said cover; said cover having a hole for access to said elastic membrane.

2. A fitting according to claim 1, wherein said first and second mouth, said cup, and said cover are made of rigid material.

3. A fitting according to claim 1, wherein said first and second mouth, said cup, and said cover are made of transparent material.

4. A fitting according to claim 1, wherein said tube extends along an axis said chamber being substantially cylindrical and having a second axis crosswise to said first axis.

5. A fitting according to claim 4, comprising a gripping member located on the opposite side of said first axis with respect to said cover.

6. A fitting according to claim 1, wherein said tube has a first diameter said chamber having a second diameter substantially larger than said first diameter.

7. A fitting according to claim 1, wherein said first and second mouth, said cup, and said tube are formed in one piece.

8. A measuring device comprising:
    a blood circulating circuit comprising a first, a second, and a third portion; said third portion being defined by a fitting comprising a first and a second mouth for connecting the fitting to said first and second portions respectively; said fitting comprising a tube configured to determine the absorption of electromagnetic waves by the blood flowing through said blood circulating circuit, said tube being made of rigid and transparent material; the fitting comprising a chamber having an elastic membrane movable as a function of the pressure of the blood flowing through said blood circulating circuit; said chamber comprising a cup formed in one piece with said tube; said chamber comprising a cover for gripping said elastic membrane between said cup and said cover;
    a seat for housing said fitting, said seat being the same shape as said fitting so as to define an unequivocal position of said fitting with respect to said measuring device when said fitting is housed in said seat;
    a pressure sensor having a first interface cooperating with said chamber, said first interface being housed in said seat; and
    a sensor configured to detect electromagnetic wave absorption, said absorption sensor having a second interface cooperating with said tube, said second interface being housed in said seat.

9. A measuring device according to claim 8, wherein said second interface surrounds said tube.

10. A measuring device according to claim 8, wherein said first interface engages a hole in said cover.

* * * * *

UNITED STATES PATENT AND TRADEMARK OFFICE
CERTIFICATE OF CORRECTION

PATENT NO. : 7,361,267 B2  Page 1 of 1
APPLICATION NO. : 10/312386
DATED : April 22, 2008
INVENTOR(S) : Annalisa Delnevo It is certified that error appears in the above-identified patent and that said Letters Patent is hereby corrected as shown below:

On the title page, item (57), line 2, "ans" should read --and--.

On the title page, item (57), line 3, "ans" should read --and--.

On the title page, item (57), line 6, "tuby" should read --tube--.

On the title page, item (57), line 7, "waved" should read --waves--.

In claim 1, column 3, line 25, "tube— and connected measuring device— configured" should read --tube and connected measuring device configured--.

In claim 4, column 3, line 43, "axis said" should read --axis, said--.

In claim 6, column 4, line 5, "diameter said" should read --diameter, said--.

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,361,267 B2  Page 1 of 1
APPLICATION NO. : 10/312386
DATED : April 22, 2008
INVENTOR(S) : Annalisa Delnevo It is certified that error appears in the above-identified patent and that said Letters Patent is hereby corrected as shown below:

On the title page, item (57), line 2, "ans" should read --and--.

On the title page, item (57), line 3, "ans" should read --and--.

On the title page, item (57), line 6, "tuby" should read --tube--.

On the title page, item (57), line 7, "waved" should read --waves--.

In claim 1, column 3, line 25, "tube— and connected measuring device— configured" should read --tube and connected measuring device configured--.

In claim 4, column 3, line 43, "axis said" should read --axis, said--.

In claim 6, column 4, line 5, "diameter said" should read --diameter, said--.

Signed and Sealed this

Nineteenth Day of August, 2008

JON W. DUDAS
*Director of the United States Patent and Trademark Office*